United States Patent [19]

Kobayashi et al.

[11] Patent Number: 4,938,071

[45] Date of Patent: Jul. 3, 1990

[54] DEVICE FOR DETECTING PROPERTIES OF SHEETS OF PAPER OF THE LIKE

[75] Inventors: Tetsuji Kobayashi; Makoto Akashi; Takahiro Yoshikawa; Shigeru Kusaka, all of Himeji, Japan

[73] Assignee: Clory Kogyo Kabushiki Kaisha, Himeji, Japan

[21] Appl. No.: 401,136

[22] Filed: Aug. 30, 1989

[30] Foreign Application Priority Data

Aug. 31, 1988 [JP] Japan .................................. 63-217298

[51] Int. Cl.⁵ .............................................. G01N 3/20
[52] U.S. Cl. ........................................ 73/849; 73/159
[58] Field of Search ................. 73/159, 849, 852, 853; 162/49, 263

[56] References Cited

U.S. PATENT DOCUMENTS 4,365,508  12/1982  Loftus .................................... 73/849
4,682,105  7/1987  Thorn ..................................... 73/159

FOREIGN PATENT DOCUMENTS 0952886  3/1964  United Kingdom .................. 73/159

Primary Examiner—Robert Raevis
Attorney, Agent, or Firm—Wenderoth, Lind & Ponack

[57] ABSTRACT

A device for detecting the degree of deterioration of bank notes has a driving rotary body and a detection rotary body, which are a pair of oppositely disposed rollers each having alternately disposed enlarged diameter portions and annular grooves. These enlarged portions and the grooves of the two rotary bodies are in staggered, opposed relationship so that when a bank note is conveyed between the two rotary bodies, the note is deformed into a wave shape. The rotation of the driving rotary body influences the rotary movement of the detection rotary body depending on the stiffness of the bank note in the wave shape. When the bank note is new and stiff, the influence is strong, while when the bank note is old and deteriorated with a small stiffness, the influence is small. Such influence is detected from variation in rotary movement of the detection rotary body to which a predetermined rotational characteristic is given by a resistance imparting device.

7 Claims, 6 Drawing Sheets

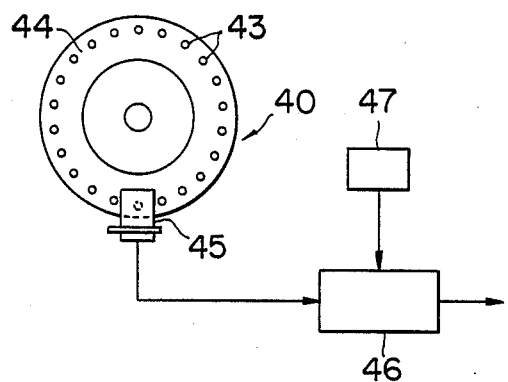
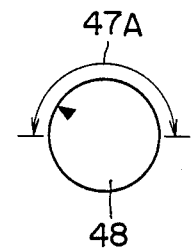
FIG. 7
FIG. 8
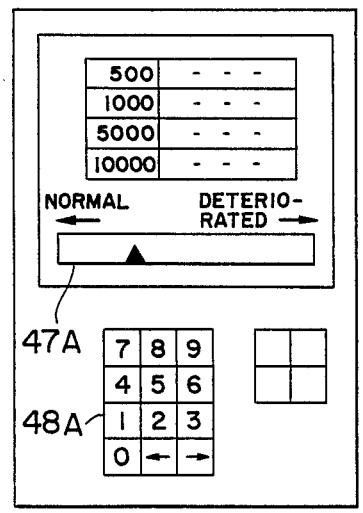
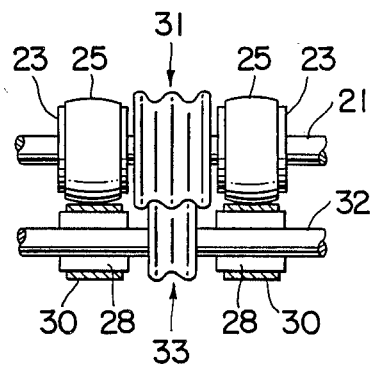
FIG. 9
FIG. 10

4,938,071

DEVICE FOR DETECTING PROPERTIES OF SHEETS OF PAPER OF THE LIKE

BACKGROUND OF THE INVENTION

The present invention relates to a device for detecting the properties such as bending resistance or stiffness of sheets of paper or the like, that are used as conditions or criteria on the basis of which it is determined whether or not bank notes or bills are genuine or they are impaired or deteriorated.

Recently, sheets of paper such as bank notes are counted, discriminated and deposited or withdrawn by various machines. Deteriorated or flaccid bank notes are not suitable for handling by such machines and must be recovered or collected during their circulation.

Some of the devices for detecting the degree of deterioration of bank notes are disclosed in, for instance Japanese Patent (Unexamined) Publication Nos. 61-168,084, 61-168,085 and 61-169,983.

The above-mentioned devices have means to produce sound by striking a sheet of paper with an elastic body, by rubbing the surface of a sheet or by conveying a sheet through a bent conveying passage so as to cause the sheet to bend, and the sound thus produced is converted into an electrical signal, which represents the degree of deterioration of sheets.

However, in the known devices, it is very difficult to pick up sound thus produced. As a result, a space in which sound is picked up must be made a completely soundproof chamber, and mechanical noises of the device must be suppressed as much as possible so that there arises the problem that the devices become very expensive. Furthermore, even when the above-mentioned problems are solved, the erroneous detection of other sounds tends to occur frequently so that there arises the problem of erroneous detection of the properties of sheets.

SUMMARY OF THE INVENTION

It is an object of the present invention to provide a device for detecting properties of sheets of paper or the like, which is simple and inexpensive but reliable in operation.

The basic principle of the device of the present invention is based on the fact that there exists a difference in stiffness between a new sheet of paper and an old sheet of paper which has been deteriorated as a result of long use.

According to the present invention, a device for detecting properties of sheets of paper comprises: driving rotary means with a moving surface having alternately disposed raised and recessed portions in a direction transverse to the direction of movement of said moving surface; means for conveying sheets of paper or the like in contact with said moving surface; detection rotary means disposed rotatably in opposed relationship with said driving rotary means and having a movable surface with alternately disposed raised and recessed portions which are in staggered, opposed relationship with the raised and recessed portions of the driving rotary means so as to form gaps between the raised portions of the driving rotary means and the raised portions of the detection rotary means, said gaps being arranged to allow the sheets fed by said means for conveying sheets to pass therethrough in a state deformed in a wave shape so that a rotary driving force is imparted from the driving rotary means to the detection rotary means through a sheet passing through said gaps; resistance imparting means for imparting to said detection rotary means a predetermined rotational characteristic such that depending upon the stiffness of the sheet passing through said gaps in the wave shape, a variation occurs in the degree to which the rotation of the driving rotary means influences the rotational characteristic of the detection rotary means, thus resulting in a variation in the rotary movement of the detection rotary means; and means for detecting the variation in the rotary movement of the detection rotary means to determine the stiffness and hence the degree of deterioration of each sheet.

In this specification, the term "a variation in rotary movement" is defined to means (1) a variation of angle of rotation, (2) a variation in the number of rotation, (3) change from a stationary state to a rotating state, (4) change from a rotating state to a stationary state (including a case in which rotation is reversed from the direction opposite to the conveyance to the direction of the conveyance so that when a sheet of paper or the like enters between the driving and detecting rotary means, the rotational speed in the direction opposite to the conveyance is decreased), and (5) a variation of rotational speed (which is different from (2) above in which time is not taken into consideration).

When a sheet of paper or the like being transported is brought into contact with the detection rotary means, a turning force corresponding to a pressure proportional to the resistance to bending of the sheet is imparted to the detection rotary means. For example, a resistance to rotation is imparted to the detection rotary means by the resistance imparting means. When the turning force is below a predetermined value, the detection rotary means is maintained in a predetermined state, but when the turning force is in excess of the predetermined value, the predetermined state of the detecting rotary means is varied in response to the turning force, and causes a variation in the rotary movement, which is detected by the means for detecting the rotary movement.

Preferred embodiments of the present invention will be described in detail hereinafter with reference to the accompanying drawings.

BRIEF DESCRIPTION OF THE DRAWINGS

FIG. 7 is a view showing a rotary movement detecting device;

FIGS. 8 and 9 are views used to explain the setting of normal and deteriorated bank notes and a display thereof;

FIG. 10 is a front view illustrating modifications of a driving rotary body and the detecting rotary body;

DETAILED DESCRIPTION OF THE PREFERRED EMBODIMENTS

Figure 1:
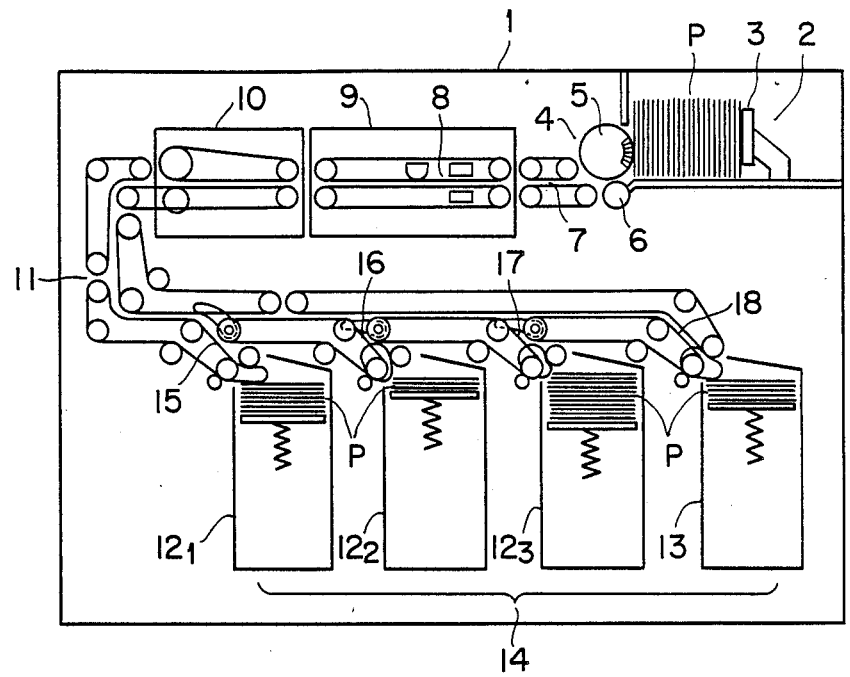
FIG. 1 is a schematic sectional view of a bank note deposition machine to which is applied the present invention.

FIG. 1 is a schematic sectional view of a bank note deposition machine to which the present invention is applied. A bank note inserting unit 2 into which the bank notes P to be deposited are put, is disposed in an upper portion of a machine housing 1. A pressing device 3 is provided to press the backmost one of a bundle of the bank notes P which are in an upright attitude so that the foremost note P is picked up by a conventional transfer device. When a kicker roller 5 and a gate roller 6 of the transfer device are rotated, the foremost note P is transferred. A conveying passage 7 made up of an upper endless running belt and a lower endless running belt is disposed downstream of the transfer device and a discrimination unit 9 with a detector 8 for detecting the denominations of the bank notes P, counterfeit notes, a note with an adhesive tape thereon and so on are disposed downstream of the conveying passage 7.

Next to the discrimination unit 9 is disposed a property detection device 10 for detecting the degree of deterioration of bank notes. The bank notes P moving out of the property detection device 10 are conveyed through a conveying passage 11. On the downstream side of the conveying passage 11 and in the lower portion of the machine housing 1 are disposed storage vessels $12_1$, $12_2$ and $12_3$ each of which stores therein bank notes P of the same denomination and an impaired or deteriorated bank note storage vessel 13 which receives bank notes discriminated as deteriorated in response to the results of detection made by the discrimination unit 9 and the property detection unit 10. These storage vessels $12_1$, $12_2$, $12_3$ and 13 constitute a bank note storage unit 14. In order to distribute the bank notes transported throughout the conveying passage into their corresponding storage vessels $12_1$, $12_2$, $12_3$ and 13, distribution passages 15, 16, 17 and 18 are arranged above the bank note storage unit 14.

Figure 2:
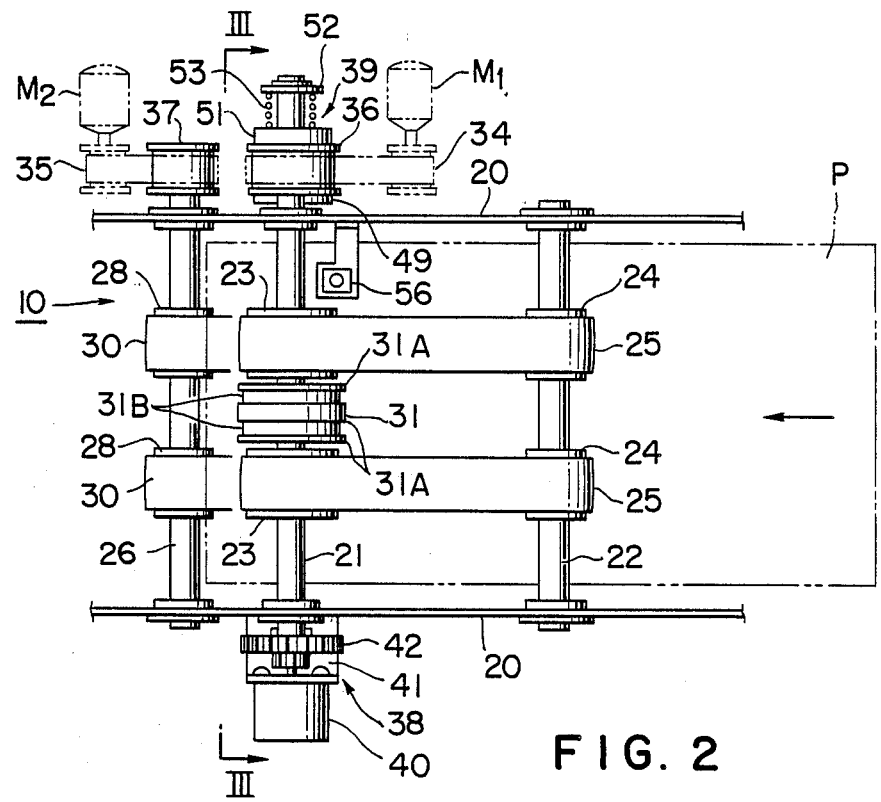
FIG. 2 is a plan view illustrating a fundamental embodiment of the present invention.
Figure 3:
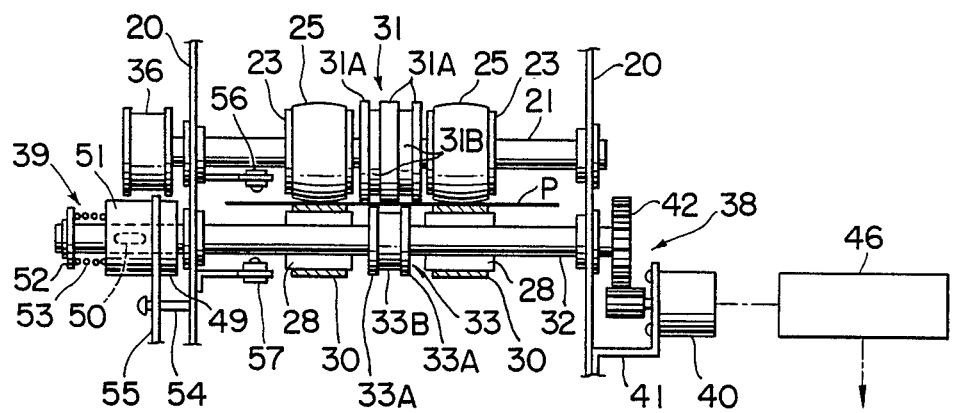
FIG. 3 is a sectional view taken along the line III—III of FIG. 2.
Figure 4:
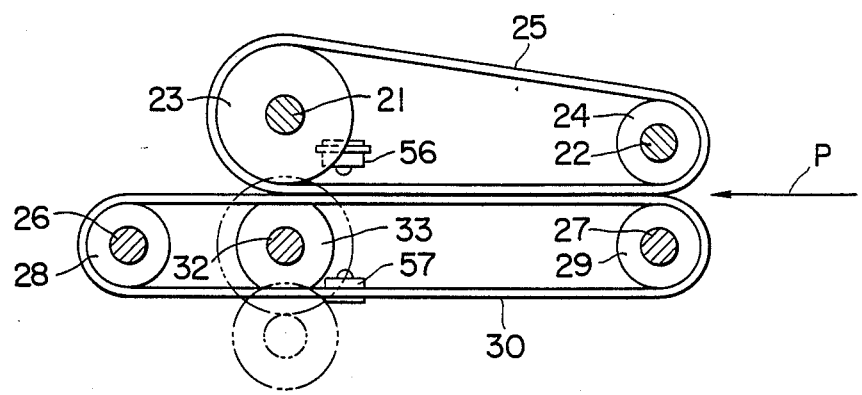
FIG. 4 is a side view of a conveying device shown in FIG. 2.

An embodiment of the property detection device 10 in accordance with the present invention is shown in FIGS. 2–4. Means for transporting sheets of paper such as bank notes comprises: pulley shafts 21 and 22 supported between members of a frame 20; pulleys 23 mounted on the shaft 21; pulleys 24 mounted on the shaft 22; two upper belts 25 passed around the pulleys 23 and 24; pulley shafts 26 and 27; pulleys 28 mounted on the shaft 26; pulleys 29 mounted on the shaft 27; and two lower belts 30 passed around the pulleys 28 and 29 in opposed relationship with the upper belts 25. The bank notes P are clamped between the upper and lower belts 25 and 30 and conveyed in the direction indicated by an arrow.

A driving rotary body 31 is securely mounted at the mid-point between the ends of the pulley shaft 21 carrying the upper belts 25, and a detection rotary body 33 is securely mounted on a shaft 32 extending immediately below the pulley shaft 21. These rotary bodies 31 and 33 are basically in the form of a roll in this embodiment.

Figures 5, 6:
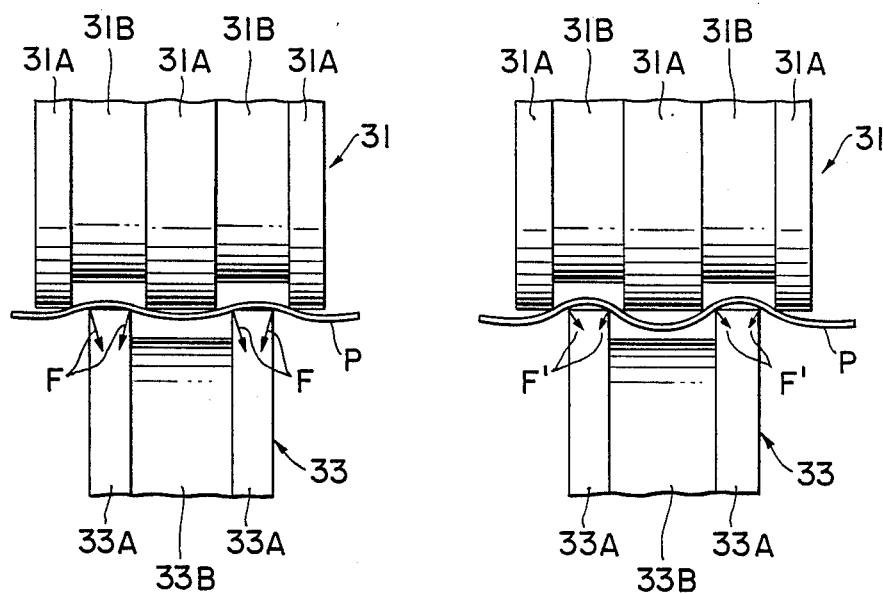
FIGS. 5 and 6 are views explaining the passages of a normal bank note and a deteriorated bank note through a property detecting device.

As shown in FIGS. 3, 5 and 6, the driving rotary body 31 has enlarged diameter portions 31A at both ends in the axial direction and at the center so that grooves 31B are defined between the enlarged diameter portion 31A on one side and the central enlarged diameter portion 31A and between the enlarged diameter portion 31A on the other side and the central enlarged diameter portion 31A. These enlarged diameter portions and grooves constitute raised and recessed portions, respectively. The detecting rotary body 33 has enlarged diameter portions 33A at both axial sides thereof of which the width is narrower than the width of the grooves 31B of the driving rotary body 31. A groove 33B is defined between the two enlarged diameter portions 33A. These portions 33A and grooves 33B also constitute raised and recessed portions, respectively.

The grooves 31B of the driving rotary body 31 are in opposing relation with the enlarged diameter portions 33A of the detection rotary body 33, respectively. Gaps for allowing the bank note P to pass therethrough is defined between the enlarged diameter portions 33A and the outer peripheral portions of the enlarged diameter portions 31A which adjoin the enlarged diameter portions 33A, so that when the bank note P passes through the gaps thus defined, it is curved in the shape of a wave between the rotary bodies 31 and 33. The enlarged diameter portions of the driving rotary body 31 and the detection rotary body 33 may be rounded as shown in FIG. 10. That is, the peripheries of the rotary bodies 31 and 33 have male-female mating relationship.

Mounted at one ends, respectively, of the pulley shafts 21 and 26 are pulleys 36 and 37 which receive the rotating forces from motors $M_1$ and $M_2$, respectively, through belts 34 and 35.

One end of the shaft 32 of the detection rotary body 33 is connected to a device 38 for detecting a variation in rotary movement, while the other end is connected to a resistance impurity device 39 for imparting resistance to rotation.

The device 38 for detecting a variation in rotary movement includes a rotary encoder 40 mounted on a mounting plate 41 which in turn is securely attached to the frame 20. The shaft 32 is connected to the encoder 40 through a connecting member (gear) 42 securely attached to one end thereof of the shaft 32. It therefore follows that variations in rotary movement of the detection rotary body can be transmitted to the encoder 40, which in turn detects the variations in rotary movement.

As shown in FIG. 7, the encoder 40 may comprise a rotary disk 44 with a plurality of small holes which are formed through the portion adjacent to the periphery of the disk in equiangularly spaced apart relationship with each other, and a sensor 45 for detecting the holes 43. The detection signal generated by the sensor 45 when the latter detects the hole 43 is delivered to a determination device 46 which has an adjustment control unit 47. As shown in FIG. 8, the control unit 47 has a knob 48 so that when the knob 48 is set at a position within the range between "NORMAL" and "DETERIORATED", a discrimination reference value is determined. That is, the property determination means 46 outputs a number of pulse signals per predetermined time interval. In this case, when the normal notes are represented by a while the deteriorated note, by b, the boundary between a and b can be selected and determined. Thus, the boundary between a and b can be suitably set. As shown in FIG. 9, in the adjustment control unit 47, the level of deterioration of the bank notes can be displayed on a display unit 47A by depressing a deterioration level setting button 48A.

Referring back to FIG. 3, the clutch device 39 for imparting resistance to rotation comprises a force receiving disk 49 fixedly mounted on the shaft 32 in the vicinity of the other end thereof, and a movable member 51 which is mounted on the shaft 32 and keyed thereto at 50 so that the movable member 51 is not permitted to rotate about the shaft 32 but is permitted to slide in the axial direction thereof. A spring seat 52 is securely attached to the other end of the shaft 32, and a compression spring 53 is loaded between the spring seat 52 and the movable member 51 for pressing the movable member 51 with a predetermined amount of force. There is provided a brake plate 55 which is fitted between the force receiving disk 49 and the movable member 51. One end of the brake plate 55 is attached to the frame 20 by means of a pin 54. Under the force of the compression spring 53, the movable member 51 is pressed against the brake plate 55 so as to impart a predetermined degree of resistance to the shaft 32. The pin 54 is fitted into an elongated hole of the brake plate 55 so that the impact caused when the bank note P enters the gaps between the driving rotary body 31 and the detection rotary body 33 can be absorbed or suppressed.

A light-emitting source 56 and a photodetector 57 are mounted on the frame 20 so that when the light beam emitted from the light source 56 to the photodetector 57 is interrupted by a bank note P, the passage of the bank note P can be detected and counting of the number of the bank notes P can be made. Furthermore, the light source 56 and the photodetector 57 are used to determine a time for picking up the signal from the encoder 40.

Next, the mode of operation of the embodiment with the above-described construction will be described.

While the foremost ones of the bundle of bank notes P placed in the bank note inserting unit 2 are transferred one by one and pass through the conveying passage 7 and the discrimination unit 9, denominations of the bank notes, counterfeit notes, overlapped notes, notes with an adhesive tape and so on are discriminated and transported to the property detection device 10. In the property detection device 10, the bank notes P are transported by the conveying device consisting of the upper and lower belts 25 and 30. Thereafter, the leading end of each bank note enters the gaps between the driving rotary body 31 and the detection rotary body 33 and is further conveyed forward.

When the bank note P is a new one and has a stiffness substantially the same as that of the bank notes as issued and when it is transported between the driving rotary body 31 and the detection rotary body 33, as shown in FIG. 5, the forces F pressing the detection rotary body 33 are great so that under these forces, the detection rotary body 33 is rotated against the resistance to rotation imparted from resistance imparting device 39, whereby the shaft 32 is rotated. A variation in the rotary movement of the shaft 32 are transmitted through the connecting member 42 to the rotary encoder 40. In response to the signal from the rotary encoder 40, the property determining means 46 decides that the bank note P is normal and to be stored in one of the storage vessels $12_1$-$12_3$ depending upon the denomination of the bank note P.

When a bank note P is deteriorated, its stiffness or resistance to bending is small. As a result, when the bank note P enters the gaps between the driving rotary body 31 and the detection rotary body 33, as shown in FIG. 6 it is easily bent to adapt itself to the contours of the enlarged diameter portions 31A and 33A of the rotary bodies 31 and 33, so that the forces F' pressing the detection rotary body 33 are small. Therefore, the detection rotary body 33 cannot overcome the resistance imparted from the resistance imparting device 39 so that the shaft 32 does not rotate or even when the detection rotary body 33 rotates by barely overcoming the resistance to rotation, a variation in rotary movement is small so that the bank note 1 is discriminated as a deteriorated or flaccid note.

Figure 11:
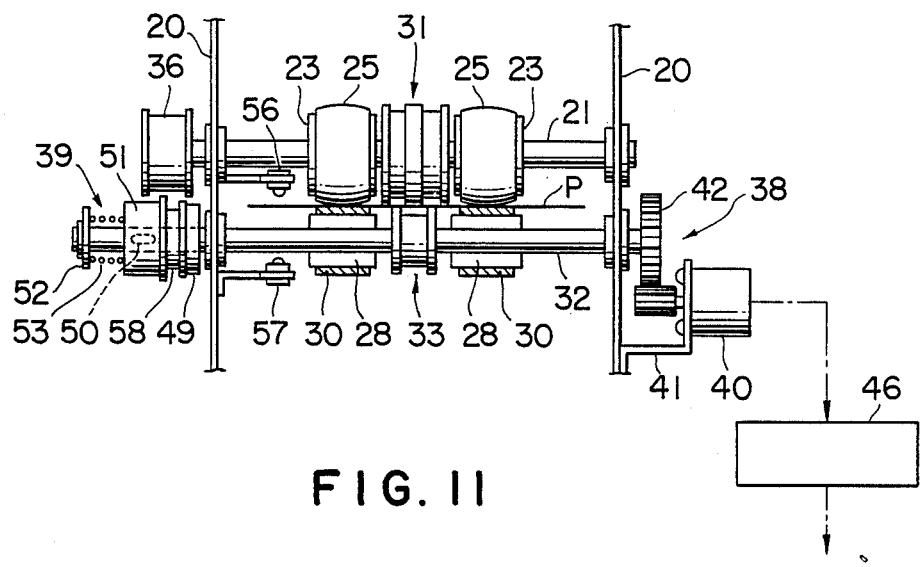
FIG. 11 is a view similar to FIG. 3 but illustrating a modification of a resistance imparting device.

FIG. 11 illustrates another example of the resistance imparting device 39 in accordance with the present invention. In this embodiment, the detection rotary body 33 is normally rotated at a peripheral speed different from the conveying speed of a bank note P. For this purpose, instead of the brake plate 55 of the first embodiment, a pulley 58 is rotatably fitted over the shaft 32 in such a manner that the side faces of the pulley 58 may be pressed against or released from the opposing axially movable member 51 and the force receiving disk 49. Under the force of the compression spring 53, the turning force transmitted to the pulley 58 from a driving belt not shown is transmitted through the force receiving disk 49 and the movable member 51 to the shaft 32, whereby the detection rotary body 33 is constantly rotated.

It therefore follows that while no bank note P enters the gaps between the rotary bodies 31 and 33, the detection rotary body 33 is rotating at a predetermined peripheral speed. When a bank note P which has a high degree of stiffness enters the gaps between the detection rotary body 33 and the driving rotary body 31, the peripheral speed of the detection rotary body 33 is decreased when a predetermined speed of the rotary body 33 is set at a value faster than the conveying speed of the bank notes. To the contrary, when the peripheral speed of the detection rotary body 33 is set at a value slower than the bank note conveying speed, the peripheral speed of the detection rotary body 33 is increased. The variation in the rotary movement is detected by the encoder 40 and the property determining device 46 discriminates it as normal. When a bank note which has a low degree of stiffness enters the gaps between the rotary bodies 31 and 33, the rotation of the detection rotary body 33 does not change or the rotation varies only a small amount, so that the bank note P is discriminated as a deteriorated flaccid note.

Next, the mode of operation of this embodiment with the above-mentioned construction will be described.

When a bank note P enters the gaps between the driving rotary body 31 and the detection rotary body 33, the bank note is conveyed while it is deformed in the shape of a wave due to the enlarged diameter portions 31A and 33A of the driving rotary body 31 and the detection rotary body 33.

In case of a new bank note P, the stiffness is so high that the restoring force is strong and acts on the detection rotary body 33 as a great vertical resistance. As a result, the peripheral speed of the detection rotary body 33 is increased (or becomes faster than the note conveying speed) or decreased (or becomes lower than the bank note conveying speed) so that the rotary movement varies greatly. The turning force imparted to the detection rotary body 33 is not limited to a positive turning force and a negative turning force may be imparted to the rotary body 33. For instance, when the detection rotary body 33 is rotating at a peripheral speed higher than the bank note conveying speed, a negative turning force is imparted in the direction of the bank note conveyance depending upon the bank note being conveyed. The variation in the rotary movement is detected by the encoder 40 and is discriminated as normal by the property determining device 46. When a deteriorated bank note P enters the gaps between the driving rotary body and the detection rotary body, its restoring force is weak because of its low stiffness so that it does not fully act to exert a vertical force to the detection rotary body 33. As a result, no variation in the rotary movement occurs, and even when some variation occurs, its amount is small; that is, the variation in the rotary movement is either none or small so that the bank note P is discriminated as a deteriorated or flaccid note.

Figure 12:
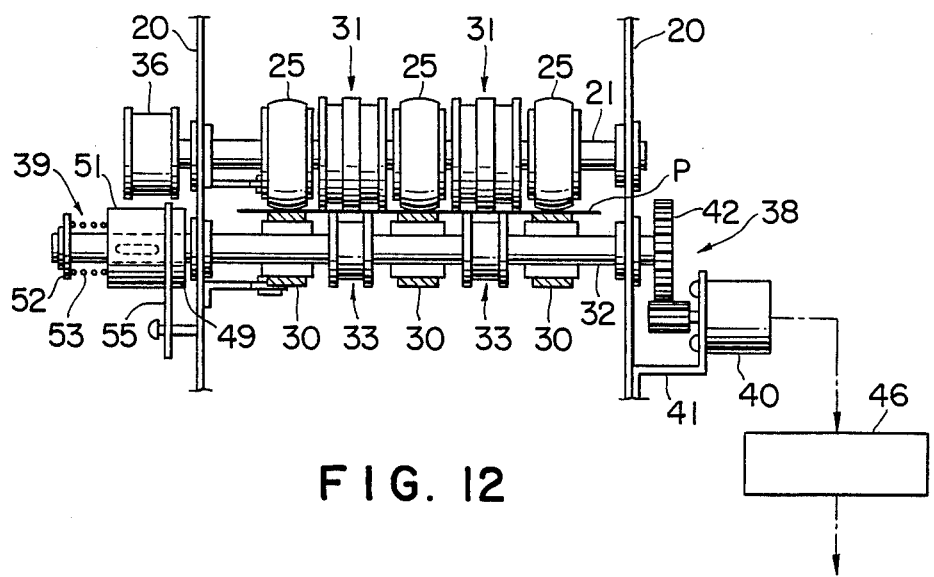
FIGS. 12 and 13 are views illustrating embodiments in which a plurality of pairs of driving rotary body and detecting rotary body are provided.

FIG. 12 shows that two pairs of driving rotary body and detection rotary body are provided in symmetrical relationship with respect to the centerline of the bank note passage, on the shafts 21 and 32.

Figure 13:
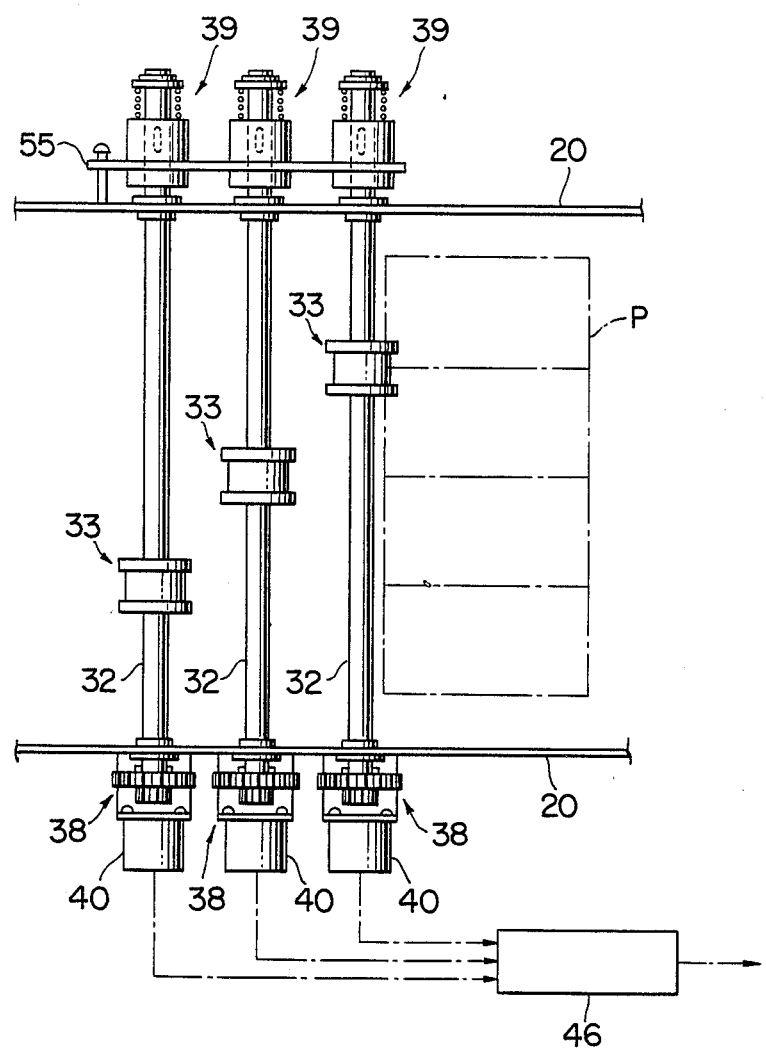

FIG. 13 illustrates an embodiment in which three pairs of driving rotary body 31 and detection rotary body pairs 33 are mounted on their respective shafts 21 and 32, respectively, in such a way that the central pair is positioned on the centerline of the bank note passage while the two other pairs are arranged with symmetrical relationship with respect to the center pair.

One of the above-described embodiments may be selected and used depending upon the kind of sheets of paper or the like to be inspected or detected. In the embodiments shown in FIGS. 12 and 13, the other arrangement of component parts is substantially the same as that of the first embodiment described above with reference to FIGS. 1-9 so that the same reference numerals are used to designate the same parts throughout the figures.

The term "determination" used in the above-described embodiments means the determination of the degree of deterioration of sheets of paper or the like, a locally abnormal thickness of sheets due to an adhesive tape or the like applied thereto, creases of the sheets, and combinations thereof. However, the device in accordance with the present invention can be used to detect only one of the degrees of deterioration of sheets of paper or the like, a locally abnormal thickness thereof, creases thereof or any combination thereof by modifying the property determination means 46 which receives signals from the device in accordance with the present invention. Furthermore, depending upon the purpose of detection, a signal from conventional or well known properties detectors and a signal from the device in accordance with the present invention may be simultaneously delivered to the property determination means 46 which is so modified as to determine the properties of the sheets of paper or the like according to the purpose of determination.

So far in the embodiments described above, both the driving rotary body 31 and the detection rotary body 33 have been described as being in the form of a roller, but it is to be understood that they may be in the form of a belt. Furthermore, it is to be understood that the sheets of paper or the like may be conveyed in the horizontal direction with the sheets being held upright, or in the vertical direction.

It is also to be understood that the present invention is not limited to the above-described embodiments and that various modification can be effected without leaving the true spirit of the present invention.

As described above, according to the present invention, in order to determine the properties of sheets of paper or the like, the degree of resistance to bending or stiffness of each sheet is detected in terms of a variation of the detection rotary body and, the variation thus detected is detected by the means for detecting a variation in the rotary movement. The result of the detection is used as the criteria for determining the properties of the sheet or for detecting whether the sheet is normal or deteriorated. As a result, regardless of the state of installation of the device, the properties of each sheet can be correctly detected. Thus the present invention can provide a device for detecting normal or impaired bank notes with a high degree of correctness at a less cost. Furthermore, the driving rotary body for causing the conveyance of sheets is disposed in opposing relationship with the detection rotary body whereby each sheet of paper or the like smoothly enters the gaps between the above two rotary bodies and that the clogging can be prevented.

What is claimed is:

1. A device for detecting properties of sheets of paper, comprising:

driving rotary means with a moving surface having alternately disposed raised and recessed portions in a direction transverse to the direction of movement of said moving surface;

means for conveying sheets of paper in contact with said moving surface;

detection rotary means disposed rotatably in opposed relationship with said driving rotary means and having a movable surface with alternately disposed raised and recessed portions which are in staggered, opposed relationship with the raised and recessed portions of the driving rotary means so as to form gaps between the raised portions of the driving rotary means and the raised portions of the detection rotary means, said gaps being arranged to allow the sheets fed by said means for conveying sheets to pass therethrough in a state deformed in a wave shape so that a rotary driving force is imparted from the driving rotary means to the detection rotary means through a sheet passing through said gaps;

resistance imparting means for imparting to said detection rotary means a predetermined rotational characteristic such that depending upon the stiffness of the sheet passing through said gaps in the wave shape, a variation occurs in the degree to which the rotation of the driving rotary means influences the rotational characteristic of the detection rotary means, thus resulting in a variation in the rotary movement of the detection rotary means; and for detecting the variation in the rotary movement detection rotary means to determine the stiffness and hence the degree of deterioration of each sheet.

2. The device as claimed in claim 1, wherein said driving rotary means is in the form of a roller, and said raised and recessed portions are enlarged diameter portions and annular grooves, respectively.

3. The device as claimed in claim 1, wherein said means for conveying sheets is a pair of mutually opposing endless belts between which the sheets are conveyed.

4. The device as claimed in claim 1, wherein said detection rotary means is in the form of a roller, and said raised and recessed portions are enlarged diameter portions and annular grooves, respectively.

5. The device as claimed in claim 1, wherein said resistance imparting means comprises a shaft supporting the detection rotary means, a force receiving disk fixedly mounted on the shaft, a movable member axially slidably mounted on the shaft to be rotatable therewith, resilient means urging the movable member toward the force receiving disk, and a stationary brake plate interposed between the force receiving disk and the movable member.

6. The device as claimed in claim 1, wherein said resistance imparting means comprises a shaft supporting the detection rotary means, a driven pulley rotatably fitted over the shaft, a force receiving disk fixedly mounted on the shaft at a position adjoining one side surface of the pulley, a movable member axially slidably mounted on the shaft to be rotatable therewith at a position adjoining the other side surface of the pulley, and resilient means urging the movable member against the pulley to provide frictional contact between the pulley and the force receiving disk and between the pulley and the movable member.

7. The device as claimed in claim 1, wherein said means for detecting the variation of the rotary movement comprises a rotary encoder connected to said detection rotary means, and property determining means receiving signals from the encoder to determine the property of the sheets.

* * * * *